US009844321B1

(12) United States Patent
Ekvall et al.

(10) Patent No.: US 9,844,321 B1
(45) Date of Patent: Dec. 19, 2017

(54) ENHANCED OPHTHALMIC SURGICAL EXPERIENCE USING A VIRTUAL REALITY HEAD-MOUNTED DISPLAY

(71) Applicant: NOVARTIS AG, Basel (CH)

(72) Inventors: Johan Ekvall, Laguna Beach, CA (US); Paul J. Essex, Rancho Santa Margarita, CA (US); Kirk Todd, Yorba Linda, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/228,357

(22) Filed: Aug. 4, 2016

(51) Int. Cl.
*A61B 3/14* (2006.01)
*A61B 3/00* (2006.01)
*A61B 3/13* (2006.01)
*A61B 90/00* (2016.01)
*G06T 19/00* (2011.01)
*G06F 3/01* (2006.01)
*A61B 90/20* (2016.01)

(52) U.S. Cl.
CPC .............. *A61B 3/13* (2013.01); *A61B 3/0025* (2013.01); *A61B 3/0058* (2013.01); *A61B 3/145* (2013.01); *A61B 90/37* (2016.02); *G06F 3/012* (2013.01); *G06T 19/006* (2013.01); *A61B 90/20* (2016.02); *A61B 2090/367* (2016.02); *A61B 2090/368* (2016.02); *A61B 2090/372* (2016.02)

(58) Field of Classification Search
CPC ........... A61B 3/13; A61B 90/37; A61B 3/145; A61B 3/0058; A61B 3/0025; A61B 2090/367; A61B 90/20; A61B 2090/372; A61B 2090/368
USPC ................................. 351/206, 246
See application file for complete search history.

*Primary Examiner* — Jack Dinh

(57) ABSTRACT

An ophthalmic surgical system comprises: a camera optically coupled to a surgical microscope; a virtual reality (VR) headset worn by a surgeon; and a VR data processing unit configured to communicate with the surgical microscope, the VR headset, and an ophthalmic surgical apparatus, wherein the VR data processing unit is configured to: project a real time video screen of video received from the camera into the VR headset; project a patient information screen into the VR headset to provide the patient information directly to the surgeon during ophthalmic surgery; project a surgical apparatus information screen into the VR headset; project a surgical apparatus input control screen into the VR headset to provide the surgeon with direct control over the surgical apparatus; and control which ones of the screens are visible in the VR headset based inputs indicating head movements of the surgeon as detected by the VR headset.

24 Claims, 3 Drawing Sheets

ENHANCED OPHTHALMIC SURGICAL EXPERIENCE USING A VIRTUAL REALITY HEAD-MOUNTED DISPLAY

FIELD

The present disclosure relates generally to ophthalmic surgery and more particularly to an enhanced ophthalmic surgical experience using a virtual reality head-mounted display.

BACKGROUND

A current surgical operating room typically involves three main personnel in a surgical procedure; the surgeon, the scrub nurse and the circulator nurse. The surgeon and scrub nurse are antiseptically sterile, the circulator nurse is not. A physical surgical apparatus is typically used that must be placed adjacent to the patient and away from the surgeon's control. In ophthalmic surgery, for example, the surgical apparatus may comprise a vitreoretinal system with posterior segment and anterior segment procedure capabilities. The surgical apparatus may include an ophthalmic microscope, a vitrectomy probe that provides high speed cutting, an illuminator, a touch panel screen having a GUI (Graphic User Interface), and an embedded laser that's controlled from a system screen on the monitor.

Currently, surgeons typically only look down the microscope into the patient's eye, and control of the surgical apparatus is done either by the surgeon using a footswitch or via verbal directions from the surgeon to a nurse who then manually interacts with the surgical apparatus using the GUI on the touch panel. All patient information (e.g., notes, images, etc.,) must be reviewed before surgery begins as it cannot be available to the surgeon in an antiseptic environment. Other types of surgery data coming from other systems or other products must be read to the surgeon or the surgeon has to take their eyes off the microscope to view the data. Consequently, the data sources used by the surgeon are separate and independent, and the flow of surgery is interrupted every time the doctor has to lift his or her head from the microscope.

Accordingly, it would be desirable to provide an improved surgical system that enhances the surgical experience for the surgeon, particularly during an ophthalmic surgery.

SUMMARY

Exemplary embodiments provide methods and systems for enhancing the ophthalmic surgical experience for the surgeon. The ophthalmic surgical system comprises: a camera optically coupled to a surgical microscope; a virtual reality (VR) headset worn by a surgeon; and a VR data processing unit configured to communicate with the surgical microscope, the VR headset, and an ophthalmic surgical apparatus for performing ophthalmic surgery on a patient, wherein the VR data processing unit is configured to: project a real time video screen of video received from the camera into the VR headset; project a patient information screen into the VR headset to provide the patient information directly to the surgeon during ophthalmic surgery; project a surgical apparatus information screen into the VR headset; project a surgical apparatus input control screen into the VR headset to provide the surgeon with direct control over the surgical apparatus; and control which ones of the screens are visible in the VR headset based inputs indicating head movements of the surgeon as detected by the VR headset.

According to the method and system disclosed herein, the exemplary embodiment provides a surgical experience whereby surgery is performed while looking into the VR headset, which projects a plurality of virtual reality surgical instrumentation screens that provide the surgeon with patient information during surgery and enable the surgeon to directly access and control the surgical apparatus, all without intervention the nurse or disruption to the flow of the surgery.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION

The exemplary embodiment relates to providing an ophthalmic surgical system that enhances the surgical experience. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

The exemplary embodiments provide an enhanced ophthalmic surgical experience for a surgeon using a virtual reality (VR) headset to improve the surgeon's access to surgical, machine and information control while performing surgery. The VR headset is used to enable the wearer (i.e. the surgeon) to directly control the surgical apparatus. Several types of VR screens may be made simultaneously available in the VR headset for display. Minimally, a high definition or ultra-high definition 3D surgical microscope video image screen is projected into the VR headset. VR screens relating to patient and machine information can be also accessed by the surgeon for presentation into the VR headset. Additional virtual surgical instrumentation screens can be viewed in the VR headset to enable the surgeon to control the physical surgical apparatuses. Navigation of the various VR screens may be performed through the surgeon's head movements or through footswitch commands.

Figure 1:
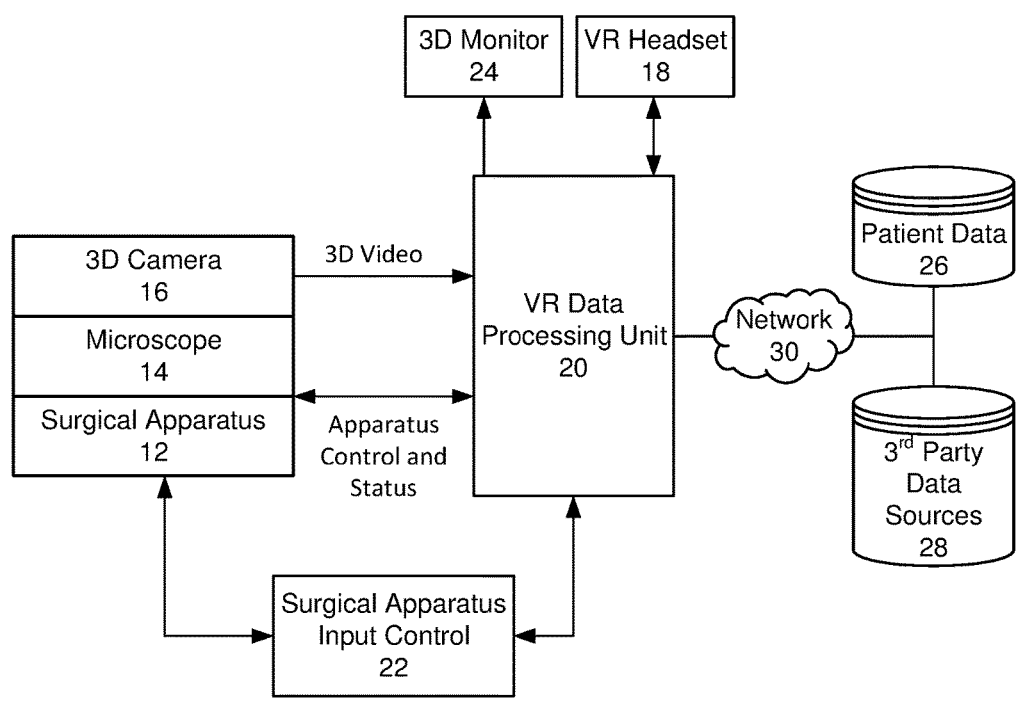
FIG. 1 is a block diagram illustrating an exemplary ophthalmic surgical system in which one embodiment of the present invention may be implemented.

FIG. 1 is a block diagram illustrating an exemplary ophthalmic surgical system in which one embodiment of the present invention may be implemented. The ophthalmic surgical system 10 may include a surgical apparatus 12, a microscope 14 coupled to the surgical apparatus, a camera (such as 3D camera 16) optically coupled to the microscope 14, a virtual reality (VR) headset 18 worn by a surgeon, and a VR data processing unit 20 communicatively coupled (via wired or wireless communication) to the surgical apparatus 12, the microscope 14, the 3D camera, and the VR headset 18. In one embodiment, the microscope 14 may comprise a 3D surgical microscope.

In one embodiment, the surgical apparatus 12 may comprise a conventional microsurgical system. For example, the surgical apparatus 12 may comprise an ophthalmic microsurgical system that is intended for one or both of anterior segment surgery (e.g., cataract surgery) and posterior segment surgery (e.g., vitreoretinal surgery). For example, in embodiments in which the surgical apparatus 12 is intended for posterior segment surgery, the surgical apparatus 12 may include a vitrectomy probe that provides high speed cutting and the ability to modify duty cycle for flow control independent of vacuum and cutting, a xenon illuminator that provides illumination for visualizing tissues, and an embedded laser.

According to one aspect of the exemplary embodiment, the surgical apparatus 12 is provided with a camera 16 mounted to the microscope 14. The surgical apparatus 12 may also be provided with both the VR data processing unit 20 and the VR headset 18, wherein the VR data processing unit 20 may be configured to project one or more virtual reality surgical instrumentation screens (VR screens) into the VR headset 18. For instance, the VR data processing unit 20 displays at least a real-time video screen of the video images from the camera 16 so that the surgeon performs surgery by looking into the VR headset 18, rather than through the microscope 14. Other virtual surgical instrumentation screens made available in the VR headset 18 during ophthalmic surgery enable the surgeon to directly control the surgical apparatus and view remotely stored patient information. These VR screens can be explored using head movement by the surgeon as detected by the VR headset 18 or with the surgical apparatus input control 22.

The VR data processing unit 20 may be coupled to the surgical apparatus 12 through a network connection, such as Ethernet, and the surgical apparatus 12 and the VR data processing unit 20 exchange apparatus control status data over the network connection. The surgery apparatus input control 22 also relays the surgeon's (and/or a nurse's) inputs to the VR data processing unit 20. In a further embodiment, the VR data processing unit 20 may be coupled to remote patient data 26 and optionally to one or more third-party data sources 28 over a wired or wireless network 30. The patient data 26 may be stored in a patient database that stores patient information and images (e.g., medical history, doctors notes, x-rays, etc.).

In operation, the camera 16 transmits 3D video of the patient's eye to the VR data processing unit 20, which passes the 3D video to the VR headset 18 for display to the surgeon. The VR data processing unit 20 may also display the 3D video from the 3D camera 16 on a monitor, such as 3D monitor 24, so that other people in the operating room may also view the 3D video of the patient's eye.

Navigation of the various VR screens may be performed through the surgeon's head movements and/or through footswitch commands. The camera 16 can be zoomed in and out under programmatic control when the surgeon moves his or her head forward or backwards using feedback from accelerometers that may be located in the VR headset. The VR headset 18 may also contain a MEMS (Microelectromechanical systems) gyroscopic sensor output that is read by the VR data processing unit 20 connected to the VR headset 18 to detect surgeon side-to-side and up-and-down head movements. These movements may be used by the VR data processing unit 20 to control which one of the VR screens is displayed in the VR headset 18 at a given time. In another embodiment, more than one VR screen may be displayed at a time by reducing the size of the VR screens.

The surgical apparatus 12 may be controlled by a surgical apparatus input control 22. In one embodiment, the surgical apparatus input control 22 may comprise an articulating touch panel screen having a GUI (Graphic User Interface) and an optional foot switch. In one embodiment, the surgical apparatus input control 22 may send the surgeons inputs to the VR data processing unit 20. Surgeon inputs can be swipes, button/switch pushes, navigation or pinch and stretch. These surgeon inputs can be manifested from the VR headset 18 through motion or gesture interpretation, surgeon eye tracking, a footswitch, a trackball and/or electroencephalographic pattern recognition.

In certain embodiments, the VR data processing unit 20 includes one or more processors and a memory. The one or more processors may be configured to execute instructions stored in the memory to cause and control the process set forth in FIG. 2 and described above. As used herein, a processor may include one or more microprocessors, field-programmable gate arrays (FPGAs), controllers, or any other suitable computing devices or resources, and memory may take the form of volatile or non-volatile memory including, without limitation, magnetic media, optical media, random access memory (RAM), read-only memory (ROM), removable media, or any other suitable memory component. Memory may store instructions for programs and algorithms that, when executed by a processor, implement the functionality described herein with respect to any such processor, memory, or component that includes processing functionality.

Figure 2:
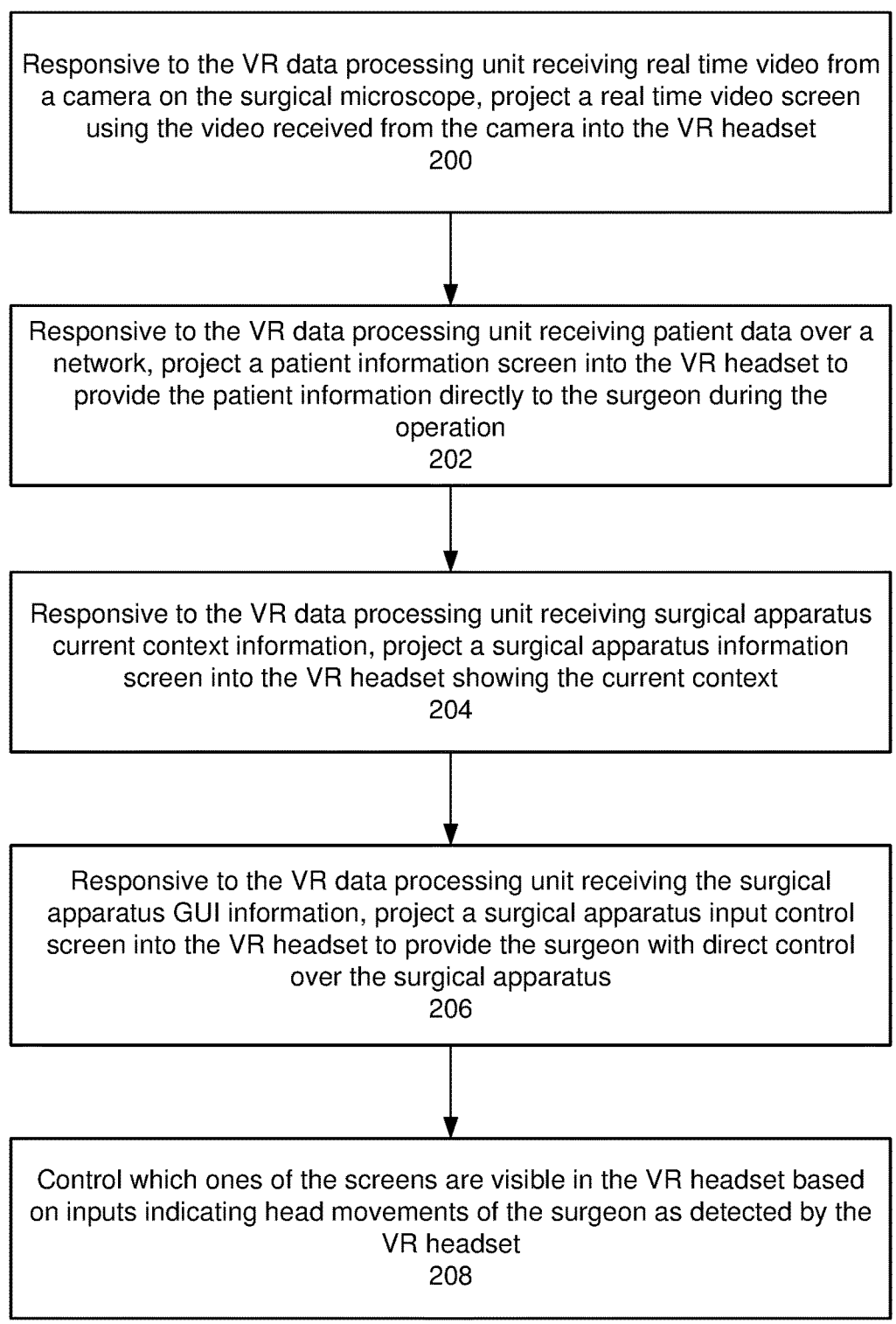
FIG. 2 is a flow diagram illustrating one embodiment of a process for providing an improved surgical experience for a surgeon using a VR headset.

FIG. 2 is a flow diagram illustrating one embodiment of a process for providing an enhanced or improved ophthalmic surgical experience for a surgeon using a VR headset 18. The purpose of using the VR headset 18 is to improve the surgeon's access to the surgical apparatus 12 and information control while performing surgery. Unless otherwise noted, the process described below is preferably performed by the VR data processing unit 20 and the processing steps may be performed in parallel, sequentially, and/or in a different order.

Responsive to the VR data processing unit 20 receiving real time video from the 3D camera 16 on the surgical microscope 14 and storing the video in one or more memories for redisplay, the VR data processing unit 20 projects a real time video screen of video received from the 3D camera into the VR headset 18 (block 200). In one embodiment, the real-time video screen may display the 3D video in high-definition or ultrahigh definition (e.g., 4k or higher).

Responsive to the VR data processing unit 20 receiving patient data 26 over a network 30, the VR data processing unit 20 projects a patient information screen into the VR headset 18 to provide the patient information directly to the surgeon during ophthalmic surgery (block 202). In one embodiment, the patient information may be stored as patient data 26 in a remote patient database and may comprise any combination of the patient's medical history, doctor's notes, x-ray and photographic images and the like.

Responsive to the VR data processing unit 20 receiving surgical apparatus current context information from the surgical apparatus 12 and storing the information in one or more memories for redisplay, the VR data processing unit 20 projects a surgical apparatus information screen into the VR headset 18 showing the current context (block 204). In one embodiment, the current context information may include device operating parameters and the like.

Responsive to the VR data processing unit 20 receiving surgical apparatus GUI information and storing the information in one or more memories for redisplay, the VR data processing unit 20 projects a surgical apparatus input control screen into the VR headset 18 that provides the surgeon with direct control over the surgical apparatus 12 (block 206). Through display of the surgical apparatus input control screen, the VR data processing unit 20 enables the surgeon to directly control the surgical apparatus 12 using at least one of: gesture interpretation, surgeon eye tracking, a footswitch, a trackball and electroencephalographic pattern recognition.

The VR data processing unit 20 is further configured to control which ones of the screens are visible in the VR headset based on inputs indicating head movements of the surgeon as detected by the VR headset (block 208). In one embodiment, sensor outputs from the VR headset 18 are sent to the VR data processing unit 20 indicating current rotation and/or inclination angles of the surgeon's head. One more software components in the VR data processing unit 20 receives the sensor outputs and detect surgeon side-to-side and up-and-down head movements. In one embodiment, each of the VR screens may be assigned a range of rotation angles and/or inclination angles that are stored in a table or the like in memory. Each VR screen may then be displayed when a match is detected between the screen's assigned rotation and/or inclination angles and the current rotation and inclination angles indicated by the sensor outputs from the VR headset 18.

Figure 3:
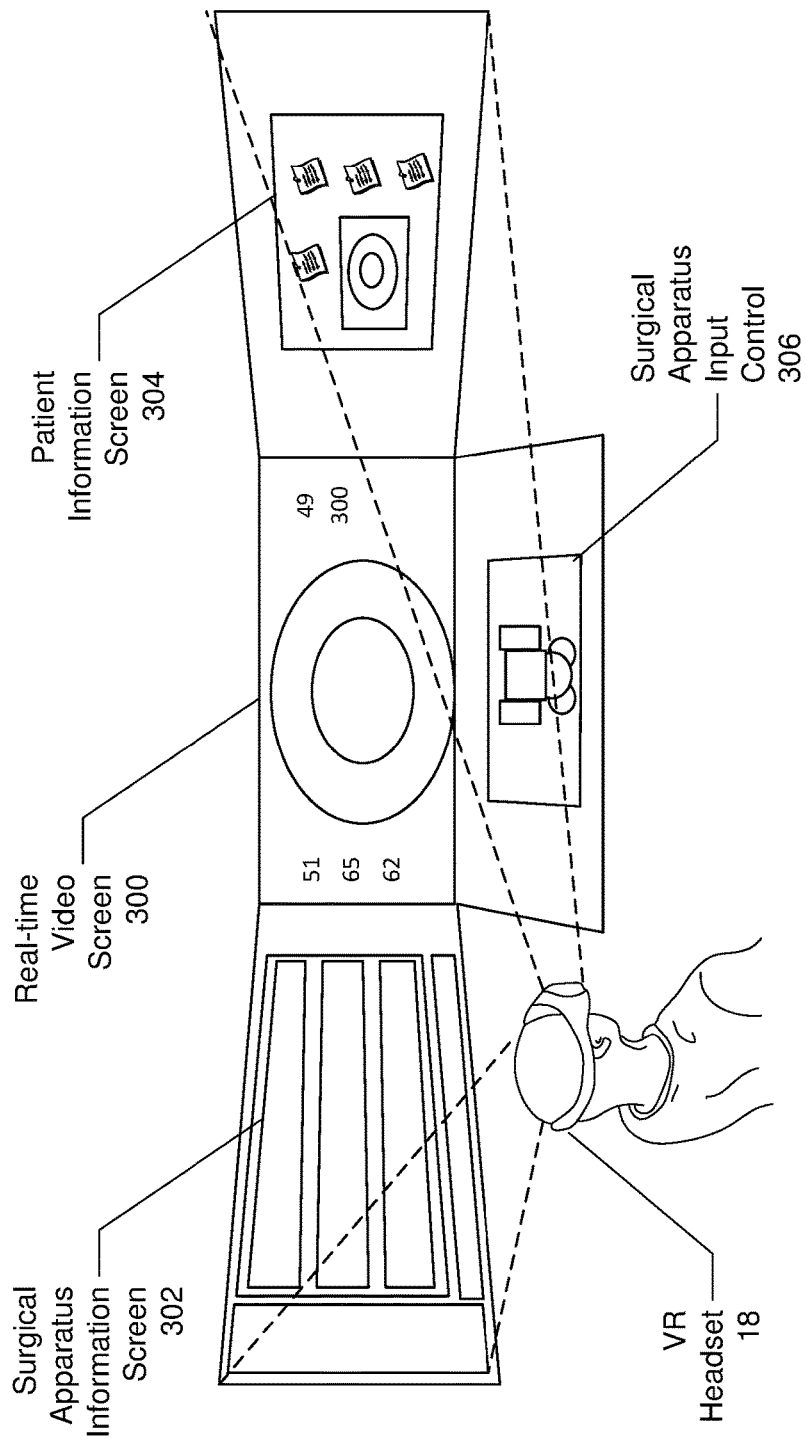
FIG. 3 is a diagram showing example of possible screens displayed in the VR headset.

FIG. 3 is a diagram showing example of possible screens displayed in the VR headset. The diagram shows the surgeon's view of the display generated by the VR data processing unit 20 while wearing the VR headset 18. As the surgeon moves his head, the VR data processing unit 20 displays different views of the virtual-reality screens. In this embodiment, the VR data processing unit 20 makes several virtual reality screens available on the display of the VR headset 18. In this specific example, the VR data processing unit 20 may make four virtual reality screens simultaneously available in the VR headset 18.

In a center portion of the field-of-view within the VR headset 18, the VR data processing unit 20 may display a real-time video screen 300 from the 3D camera. On the left, the VR data processing unit 20 may display a surgical apparatus information screen 302 from the surgical apparatus input control 22 showing surgical apparatus current context. On the right, the VR data processing unit 20 may display a patient information screen 304, which may include pre-operation data and images and doctor notes for surgeon reference during the operation. On the bottom, the VR data processing unit 20 may display a surgical apparatus input control screen 306 that enables the surgeon to directly control the surgical apparatus 12. Other screens may be generated and displayed by the VR data processing unit 20, such as a video image of the operating room via an operating room camera, or any other relevant data or function having to do with the operating room, e.g. anesthesiology information.

According to one feature of the exemplary embodiment, the plurality of VR screens projected into the VR headset 18 provide the surgeon with virtually unlimited information during surgery and enables the surgeon to directly access and control the surgical apparatus 12 without intervention of a nurse. The virtual nature of these VR screens allows a perceived proximity to the surgeon that would be physically impossible with un-augmented normal human perception. The use of VR screens in the VR headset 18 eliminates the physical limitations imposed by the size of the surgical apparatus and the antiseptic limitations for information sharing.

A method and system for providing an enhanced surgical experience for a surgeon using a VR headset has been disclosed. The present invention has been described in accordance with the embodiments shown, and there could be variations to the embodiments, and any variations would be within the spirit and scope of the present invention. For example, the exemplary embodiment can be implemented using hardware, software, a computer readable medium containing program instructions, or a combination thereof. Software written according to the present invention is to be either stored in some form of computer-readable medium such as a memory, a hard disk, or a CD/DVD-ROM and is to be executed by a processor. Accordingly, many modifications may be made by one of ordinary skill in the art without departing from the spirit and scope of the appended claims.

We claim:

1. An ophthalmic surgical system, comprising:
   a 3D camera optically coupled to a surgical microscope;
   a virtual reality (VR) headset worn by a surgeon; and
   a VR data processing unit configured to communicate with the 3D camera, the VR headset, and an surgical apparatus for performing ophthalmic surgery on a patient, wherein the VR data processing unit is configured to:
      project a real time video screen of video received from the 3D camera into the VR headset;
      project a patient information screen into the VR headset to provide the patient information directly to the surgeon during ophthalmic surgery;
      project a surgical apparatus information screen into the VR headset showing a current context of the surgical apparatus;
      project a surgical apparatus input control screen into the VR headset that provides the surgeon with direct control over the surgical apparatus; and
      control which ones of the real time video screen, the patient information screen, the surgical apparatus information screen, and the surgical apparatus input control screen are visible in the VR headset based inputs indicating head movements of the surgeon as detected by the VR headset.

2. The system of claim 1, wherein the surgeon is provided with control over the surgical apparatus from the VR headset through at least one of:
   gesture interpretation;
   surgeon eye tracking;
   a footswitch;
   a trackball; and
   electroencephalographic pattern recognition.

3. The system of claim 1, wherein the VR data processing unit is further configured to:
receive feedback from accelerometers located in the VR headset indicating forward or backward movement of the surgeon's head; and
adjust the zoom of the 3D camera based on the received feedback.

4. The system of claim 1, wherein the VR data processing unit controls which ones of the real time video screen, the patient information screen, the surgical apparatus information screen, and the surgical apparatus input control screen are visible in the VR headset by:
receiving sensor outputs from the VR headset; and
determining, based on the received sensor outputs, surgeon side-to-side and up-and-down head movements.

5. The system of claim 1, wherein:
each of the real time video screen, the patient information screen, the surgical apparatus information screen, and the surgical apparatus input control screen is assigned a corresponding range of rotation angles and/or inclination angles; and
the VR data processing controls which ones of the real time video screen, the patient information screen, the surgical apparatus information screen, and the surgical apparatus input control screen are visible in the VR headset by:
receiving sensor outputs from the VR headset indicating a measured rotation angle and/or inclination angle of the surgeon's head; and
displaying each of the screens having a corresponding range of rotation angles and/or inclination angles covering the measured rotation angle and/or inclination angle of the surgeon's head.

6. The system of claim 1, wherein the patient information displayed on the patient information screen comprises any combination of a patient's medical history, doctor's notes, and images.

7. The system of claim 1, wherein the current context of the surgical apparatus includes device operating parameters.

8. The system of claim 1, wherein the VR data processing unit is further configured to display the video received from the 3D camera on a monitor located in an operating room.

9. A method for providing an enhanced ophthalmic surgical experience for a surgeon, the method comprising:
responsive to a VR data processing unit receiving real time video from a 3D camera optically coupled to a surgical microscope, projecting, by the VR data processing unit, a real time video screen of the video received from the 3D camera into a VR headset;
responsive to the VR data processing unit receiving patient data over a network, projecting, by the VR data processing unit, a patient information screen into the VR headset during ophthalmic surgery;
responsive to the VR data processing unit receiving surgical apparatus current context information from an surgical apparatus for performing ophthalmic surgery on the patient, projecting, by the VR data processing unit, a surgical apparatus information screen into the VR headset showing the current context of the surgical apparatus;
responsive to the VR data processing unit receiving surgical apparatus information, projecting, by the VR data processing unit, a surgical apparatus input control screen into the VR headset that provides the surgeon with direct control over the surgical apparatus; and
controlling, by the VR data processing unit, which ones of the real time video screen, the patient information screen, the surgical apparatus information screen, and the surgical apparatus input control screen are visible in the VR headset based inputs indicating head movements of the surgeon as detected by the VR headset.

10. The method of claim 9, wherein the surgeon is provided with control over the surgical apparatus from the VR headset through at least one of:
gesture interpretation;
surgeon eye tracking;
a footswitch;
a trackball; and
electroencephalographic pattern recognition.

11. The method of claim 9, further comprising, responsive to the VR data processing unit receiving feedback from accelerometers located in the VR headset indicating forward or backward movement of the surgeon's head, adjusting the zoom of the 3D camera based on the received feedback.

12. The method of claim 9, wherein the VR data processing unit controls which ones of the real time video screen, the patient information screen, the surgical apparatus information screen, and the surgical apparatus input control screen are visible in the VR headset by:
receiving sensor outputs from the VR headset; and
determining, based on the received sensor outputs, surgeon side-to-side and up-and-down head movements.

13. The method of claim 9, wherein:
each of the real time video screen, the patient information screen, the surgical apparatus information screen, and the surgical apparatus input control screen is assigned a corresponding range of rotation angles and/or inclination angles; and
the VR data processing controls which ones of the real time video screen, the patient information screen, the surgical apparatus information screen, and the surgical apparatus input control screen are visible in the VR headset by:
receiving sensor outputs from the VR headset indicating a measured rotation angle and/or inclination angle of the surgeon's head; and
displaying each of the screens having a corresponding range of rotation angles and/or inclination angles covering the measured rotation angle and/or inclination angle of the surgeon's head.

14. The method of claim 9, wherein the patient information displayed on the patient information screen comprises any combination of a patient's medical history, doctor's notes, and images.

15. The method of claim 9, wherein the current context of the surgical apparatus includes device operating parameters.

16. The method of claim 9, further comprising displaying, by VR data processing unit, the video received from the 3D camera on a monitor located in an operating room.

17. A non-transitory computer-readable medium containing program instructions for providing an enhanced ophthalmic surgical experience for a surgeon, the program instructions for:
responsive to a VR data processing unit receiving real time video from a 3D camera optically coupled to a surgical microscope, projecting, by the VR data processing unit, a real time video screen of the video received from the 3D camera into a VR headset;
responsive to the VR data processing unit receiving patient data over a network, projecting, by the VR data processing unit, a patient information screen into the VR headset during ophthalmic surgery;
responsive to the VR data processing unit receiving surgical apparatus current context information from an surgical apparatus for performing ophthalmic surgery on the patient, projecting, by the VR data processing unit, a surgical apparatus information screen into the VR headset showing the current context of the surgical apparatus;

responsive to the VR data processing unit receiving surgical apparatus information, projecting, by the VR data processing unit, a surgical apparatus input control screen into the VR headset that provides the surgeon with direct control over the surgical apparatus; and controlling, by the VR data processing unit, which ones of the real time video screen, the patient information screen, the surgical apparatus information screen, and the surgical apparatus input control screen are visible in the VR headset based inputs indicating head movements of the surgeon as detected by the VR headset.

18. The non-transitory computer-readable medium of claim 17, wherein the surgeon is provided with control over the surgical apparatus from the VR headset through at least one of:

gesture interpretation;
surgeon eye tracking;
a footswitch;
a trackball; and
electroencephalographic pattern recognition.

19. The non-transitory computer-readable medium of claim 17, the program instructions additionally for, responsive to the VR data processing unit receiving feedback from accelerometers located in the VR headset indicating forward or backward movement of the surgeon's head, adjusting the zoom of the 3D camera based on the received feedback.

20. The non-transitory computer-readable medium of claim 17, wherein the VR data processing unit controls which ones of the real time video screen, the patient information screen, the surgical apparatus information screen, and the surgical apparatus input control screen are visible in the VR headset by:

receiving sensor outputs from the VR headset; and
determining, based on the received sensor outputs, surgeon side-to-side and up-and-down head movements.

21. The non-transitory computer-readable medium of claim 17, wherein:

each of the real time video screen, the patient information screen, the surgical apparatus information screen, and the surgical apparatus input control screen is assigned a corresponding range of rotation angles and/or inclination angles; and the VR data processing controls which ones of the real time video screen, the patient information screen, the surgical apparatus information screen, and the surgical apparatus input control screen are visible in the VR headset by:

receiving sensor outputs from the VR headset indicating a measured rotation angle and/or inclination angle of the surgeon's head; and displaying each of the screens having a corresponding range of rotation angles and/or inclination angles covering the measured rotation angle and/or inclination angle of the surgeon's head.

22. The non-transitory computer-readable medium of claim 17, wherein the patient information displayed on the patient information screen comprises any combination of a patient's medical history, doctor's notes, and images.

23. The non-transitory computer-readable medium of claim 17, wherein the current context of the surgical apparatus includes device operating parameters.

24. The non-transitory computer-readable medium of claim 17, further comprising displaying, by VR data processing unit, the video received from the 3D camera on a monitor located in an operating room.

* * * * *